United States Patent [19]

Matthes et al.

[11] Patent Number: 4,577,045

[45] Date of Patent: Mar. 18, 1986

[54] METHOD FOR THE PRODUCTION OF ANHYDROUS POTASSIUM TERT.BUTOXIDE

[75] Inventors: Reinhard Matthes, Rheinfelden; Hans-Joachim Vahlensieck, Wehr, both of Fed. Rep. of Germany

[73] Assignee: Dynamit Nobel AG, Cologne, Fed. Rep. of Germany

[21] Appl. No.: 714,369

[22] Filed: Mar. 21, 1985

[30] Foreign Application Priority Data

Apr. 7, 1984 [DE] Fed. Rep. of Germany ....... 3413212

[51] Int. Cl.$^4$ .............................................. C07C 29/70
[52] U.S. Cl. ..................................................... 568/851
[58] Field of Search ......................................... 568/851

[56] References Cited

U.S. PATENT DOCUMENTS

| | | | |
|---|---|---|---|
| 1,712,830 | 5/1929 | Kyrides | 568/851 |
| 1,816,843 | 8/1931 | Halbig et al. | 508/851 |
| 1,910,331 | 5/1933 | Halbig | 568/851 |
| 2,877,274 | 3/1959 | Kramis | 568/851 |
| 3,418,383 | 12/1968 | Lenz et al. | 568/851 |
| 4,327,230 | 4/1982 | Ackermann et al. | 568/851 |
| 4,421,936 | 12/1983 | Smith et al. | 568/851 |

FOREIGN PATENT DOCUMENTS 639848   4/1979   U.S.S.R. ............................... 568/851

*Primary Examiner*—J. E. Evans
*Attorney, Agent, or Firm*—Felfe & Lynch

[57] ABSTRACT

Disclosed is a method for continuous production of anhydrous potassium tert.butoxide from aqueous potash lye and tert.butyl alcohol in a packed distillation column. The water of reaction and the water brought in by the starting products is distilled out at the top of the column with the aid of a withdrawing agent. In the bottom of the column an alcoholic solution of the potassium tert.butoxide is produced, which is withdrawn and then processed for isolation of the anhydrous salt. The tert.butyl alcohol is used in excess such that a 10 to 18 weight-percent solution of the salt in alcohol is produced in the bottom of the column. The amount of tert.butyl alcohol together with the amount of the withdrawing agent is selected such that the tert.butyl alcohol content in the gas mixture at the center of the column will be between 50 and 90% by weight. The bottom of the column is continuously maintained at ebullition. A gas mixture of 20 to 50 wt. -% of tert.butyl alcohol and 50 to 80 wt. -% of the withdrawing agent is withdrawn from the top of the column at a temperature between 65° and 75° C. Cyclohexane or hexane is used as withdrawing agent in accordance with the invention.

4 Claims, No Drawings

METHOD FOR THE PRODUCTION OF ANHYDROUS POTASSIUM TERT.BUTOXIDE

BACKGROUND OF THE INVENTION

The subject matter of the present invention is a method for the production of anhydrous potassium tert.butoxide by the reaction of aqueous potash lye with tert.butyl alcohol in a packed distillation column, in which the water is distilled out at the top using a withdrawing agent, and in the sump of the column, which is kept at the boiling temperature, an alcoholic solution of the potassium tert.butoxide is produced, which is continuously withdrawn and is then processed for the recovery of the potassium salt.

The preparation of potassium tert.butoxide, which is generally called potassium tert.butylate, from metallic potassium with anhydrous tert.butyl alcohol, is described in Houben-Weyl, Vol. IV/2 (1963), pp. 7-8, where mention is also made of the possibility of operating in an inert solvent. This procedure, however, has the disadvantage that the metallic potassium used is difficult to handle, and that the absolutely water-free tertiary butyl alcohol that is needed to achieve an end product of perfect quality is difficult to produce.

Even in the case of the known transalcoholization of a lower alcoholate with the desired higher alcohol, it is necessary, in order to produce anhydrous potassium tert.butoxide, to have an absolutely water-free tert.butyl alcohol, which is very difficult to produce in pure form. Also, in the case of the transalcoholization of lower potassium alcoholates with tert.butyl alcohol, the equilibrium is very strongly on the side of the starting substances, so that only a great excess of tert.butyl alcohol will lead to reasonable yields. This excess necessitates the boiling up of large amounts of butanol, which considerably increases the expenditure of energy required by this process.

The above disadvantages are largely removed by the process described in German Federal Pat. No. 968,903: the reaction water is distilled azeotropically and thus removed from the system. This process, however, has the disadvantage that, in the preparation of potassium tert.butoxide, the incrustations of solid potassium hydroxide that form on the column packings can lead to the clogging of the column. This disadvantage can be remedied by the use of small amounts of caustic potash solution, but this considerably reduces the yield.

The procedure described in German Federal Pat. No. 968,903 does mention azeotropic distillation of the alcohol by means of a withdrawing agent. In the process described therein, however, the alcohol of the water-alcohol azeotrope that is distilled out must be constantly replaced, and a complex recovery process is necessary for that purpose.

The problem therefore existed of conducting the production of anhydrous potassium tert.butoxide from caustic potash solution and tert.butyl alcohol such that the reaction can be performed continuously in a distillation column without clogging or incrustation, and the unreacted input substances can be recovered in a simple manner. Furthermore, in the new process a very pure end product is to be obtained, whose KOH content is as low as possible, preferably less than 1% by weight.

THE INVENTION

For the achievement of this object a process has been found for the production of anhydrous potassium tert-.butoxide by the reaction of aqueous caustic potash solution with tert.butyl alcohol in a packed distillation column, removal of the water by distillation using a withdrawing agent, and withdrawal of the alcoholic solutions of potassium tert.botoxide from the bottom of the column, the anhydrous salt being isolated from this withdrawn solution in a known manner.

The inventive process includes
 (a) using cyclohexane or hexane as withdrawing agent,
 (b) using the tert.butyl alcohol in such an excess with respect to the aqueous potash lye and the withdrawing agent that in the bottom of the column a 10 to 18 wt.-% solution of potassium tert.butoxide is present, and the content of tert.butyl alcohol in the gas mixture situated in the center of the column is between 50 and 90 wt.-%, and
 (c) distilling out a mixture of withdrawing agent, tert.butyl alcohol and water at temperatures between 65° and 75° C.

When the process of the invention is performed, no clogging occurs in the distillation, and the alcohol can be recycled to the process almost completely, without complex processing. A pure, anhydrous product is obtained, whose KOH content is less than 1% by weight.

The aqueous caustic potash solution used in the process can best be a concentrated lye from which solid KOH does not precipitate at the reaction temperatures. Lyes having KOH contents of about 50% by weight can be used; the KOH content can be even lower, but then correspondingly larger amounts of water have to be distilled out. For this reason the use of potash lyes of KOH contents under 30 weight-percent is not recommended.

The tertiary butyl alcohol does not have to be absolutely anhydrous in the process of the invention. Water contents under 11.76% (composition of the tert.butyl alcohol/water azeotrope) virtually do not interfere with the process of the invention. Preferably, however, the tert.butyl alcohol is to have a water content of less than 0.1% by weight.

The tert.butyl alcohol is not only reacting agent, it serves simultaneously as solvent for the potassium butoxide obtained, up to 90% by weight of total tert.butyl alcohol amount. Less than 1% by weight of total tert. butyl alcohol is part of the aqueous phase. Therefore the amount of the tert.butyl alcohol needed for the whole process should be sufficiently great that a 10 to 18% by weight, preferably a 10 to 15% by weight, solution of the potassium salt will be present in the bottom of the distillation column.

The amount of the tert.butyl alcohol is furthermore to be selected such that, at the boiling temperature in the bottom, the content of tert.butyl alcohol in the gas mixture at the center of the column will be between 50 and 90% by weight. The remaining part of the gas mixture there consists mostly of cyclohexane or hexane. The amount of the hexane or cyclohexane must accordingly be selected such that the above-named content will be present in the gas mixture in the center of the column (that means: approximately at half the height of the column).

The tert.butyl alcohol is generally used in liquid form and delivered to the top of the column.

When a part of the tert.butyl alcohol used as solvent is replaced by cyclohexane or hexane, the contents of hexane or cyclohexane in the gas mixture are accordingly higher and the solvent for the potassium tert-butoxide in the sump of the column consists partially also of cyclohexane or hexane.

The above-described conditions for the amounts of tert.butyl alcohol to be used are satisfied generally if the alcohol is used in 6 to 20 times, preferably 9 to 20 times, the volume of the aqueous potash lye.

If the composition of the gas mixture at the center of the column and the concentration of potassium tert-butoxide in the bottom of the column at ebullition are in accordance with the invention, the result will be a gas mixture at the top of the column consisting of 20 to 50% by weight of tert.butyl alcohol by weight and 50 to 80% by weight of cyclohexane or hexane by weight, and of water vapor. Depending on the water content of the mixture, the top temperature will be between 65 and 75° C. (if hexane is used instead of cyclohexane, 59° to 69° C.); the water content of the mixture will thus be generally less than the amount corresponding to the ternary azeotrope, cyclohexane/tert.butylalcohol/water, which has a boiling point of 65° C. (if hexane is used instead of cyclohexane the boiling point will be 59° C.). The mixture leaving the top within the named temperature range (accordingly not a pure azeotrope) is best condensed, separating into an aqueous phase and an organic phase.

The aqueous phase contains both the water contained in the starting products and the water formed by the reaction. In this phase tert.butyl alcohol can be contained in solution up to a content of 10% by weight.

The organic phase passing through the top of the column is best recycled, preferably to the top of the distillation column, after it is condensed. It contains mostly the withdrawing agent and the part of the distilled tert.butyl alcohol that is not dissolved in the water.

In the column, the reaction product that forms therein and is dissolved in the tert.butyl alcohol/hexane or cyclohexane mixture is washed into the bottom of the column, which is kept at the boiling temperature throughout the reaction. The potassium tert.butoxide is then in the bottom in the form of a 10 to 18% solution in pure, anhydrous tert.butyl alcohol. Preferably, the concentration of the potassium salt in the tert.butyl alcohol amounts to 10 to 15% by weight.

The potassium tert.butoxide solution is withdrawn from the bottom of the column continuously, preferably through an overflow, and then the potassium salt is isolated in a manner known in itself, e.g., by distilling out the alcohol in vacuo. It precipitates as a while, finely granular, hygroscopic powder of high purity.

In an alternate embodiment of the invention, tert.butyl alcohol is delivered into the center of the column in vapor form in the amount of 9 to 20 times the volume of the aqueous KOH, while the rest of the procedure is similar. In this manner the throughput and hence the capacity can be increased.

In another alternate embodiment of the invention, as much as half of the volume of tert.butyl alcohol is replaced by cyclohexane or hexane, and the mixture of these solvents is delivered to the top of the column. In this manner, potassium tert.butoxide is obtained in the solution of a mixture of tert.butyl alcohol and cyclohexane (or hexane) and isolated in the manner described above. This method of procedure has a positive effect on mechanical property (particle size) of the product and facilitates drying. In this procedure, too, the solvents distilled from the bottom of the column can be recycled to the synthesis.

EXAMPLE 1

The reaction was performed in a continuously running distillation column, nominal width 50 mm, with an effective packed height of 8 m. The column was packed with V4A packing which was characterized by a large surface area and good separating action. The bottom of the column was equipped with an overflow from which the product solution was withdrawn. The top of the column was provided with a separator which permitted the separation of the aqueous phase and recycled the organic phase to the top of the column.

Before the reaction began, a mixture of tert.butyl alcohol and cyclohexane was brought to ebullition in the bottom of the column, so that an equilibrium of the two components established itself in the column. The composition of the starting mixture was selected such that, after equilibrium was established, the condensate in the center of the column still contained about 30 weight-percent of cyclohexane. In this preparatory phase the water contained in traces in the mixture was already separated. If the column is prepared in this manner, the reaction is begun. With the continuous delivery per hour of 18.5 g of 50% potash lye and 117 g of tert.butyl alcohol with a moisture content of less than 0.05% to the top of the column, an approximately 15% solution was obtained of potassium tert. butoxide in tert.butyl alcohol. The solution was greatly concentrated in the rotary evaporator at 40° C. and 100 mbar, and the final drying took place at 160° C. and 10 mbar. The end product was a white, finely granular powder whose KOH content amounts to 0.4%.

EXAMPLE 2

The experiment was performed the same as in Example 1, but with hexane instead of cyclohexane. With an hourly input of 17.3 g of 50% KOH and 103 g of tert.butyl alcohol, moisture content less than 0.05%, an approximately 16% product solution was obtained. The end product contained after drying, 0.8% of KOH.

EXAMPLE 3

The experiment was performed as in Example 1, but 50 volume-percent of the amount of tert.butyl alcohol is replaced by cyclohexane. With an hourly input of 10 g of 50% potash lye and 72 g of a mixture of 36 g of cyclohexane and 36 g of tert.butyl alcohol, a product solution of approximate 11% was obtained. After drying the end product contained 0.6% KOH.

It will be understood that the specification and examples are illustrative but not limitative of the present invention and that other embodiments within the spirit and scope of the invention will suggest themselves to those skilled in the art.

We claim:

1. A method for continuous production of anhydrous potassium tert.butoxide comprising
   reacting aqueous potash lye with tert.butyl alcohol in a packed distillation column, and removing water by distillation using cyclohexane and/or hexane as withdrawing agent,
   the tert.butyl alcohol being present in such excess of the aqueous potash lye and the withdrawing agent such that there is a 10 to 18 wt.-% solution of potassium tert.butoxide in the column bottom and the tert.butyl alcohol of the gas mixture at the center of the column is between 50 and 90 wt.-%; distilling out a mixture of the withdrawing agent, tert.butyl alcohol and water at the column top at temperatures of between 65° and 75° C.;

withdrawing the solution of potassium tert.butoxide produced in the column bottom; and obtaining anhydrous potassium tert.butoxide from the withdrawn solution.

2. The method of claim 1, wherein the mixture at the top of the column is separated into an aqueous phase and an organic phase and the organic phase is fed back into the column.

3. The method of claim 1, wherein the tert.butyl alcohol is fed in vapor form to the upper part of the column, preferably to the center of the column.

4. The method of claim 1, wherein up to 50% of the tert.-butyl alcohol is replaced by cyclohexane or hexane.

* * * * *